US008901492B1

(12) United States Patent
Cheng et al.

(10) Patent No.: US 8,901,492 B1
(45) Date of Patent: Dec. 2, 2014

(54) THREE-DIMENSIONAL SEMICONDUCTOR IMAGE RECONSTRUCTION APPARATUS AND METHOD

(71) Applicant: Taiwan Semiconductor Manufacturing Company, Ltd., Hsin-Chu (TW)

(72) Inventors: Wen-Hao Cheng, Hsin-Chu (TW); Ajay Nandoriya, Hsin-Chu (TW); Chung-Min Fu, Chungli (TW); Chih-Chiang Tu, Tauyen (TW)

(73) Assignee: Taiwan Semiconductor Manufacturing Company, Ltd., Hsin-Chu (TW)

( * ) Notice: Subject to any disclaimer, the term of this patent is extended or adjusted under 35 U.S.C. 154(b) by 0 days.

(21) Appl. No.: 14/015,383

(22) Filed: Aug. 30, 2013

Related U.S. Application Data

(60) Provisional application No. 61/846,950, filed on Jul. 16, 2013.

(51) Int. Cl.
G01N 23/203 (2006.01)
H01J 37/28 (2006.01)
(52) U.S. Cl.
CPC .............. G01N 23/203 (2013.01); H01J 37/28 (2013.01); H01J 2237/2815 (2013.01); H01J 2237/2818 (2013.01)
USPC ........................................................ 250/307

(58) Field of Classification Search
USPC .................................................. 250/306–310
See application file for complete search history.

(56) References Cited

U.S. PATENT DOCUMENTS

| 6,812,462 | B1 * | 11/2004 | Toth et al. | 850/1 |
| 8,189,903 | B2 * | 5/2012 | Itoh | 382/144 |
| 2005/0285034 | A1 * | 12/2005 | Tanaka et al. | 250/310 |
| 2013/0037716 | A1 * | 2/2013 | Tadaka et al. | 250/307 |
| 2013/0200255 | A1 * | 8/2013 | Schwarzband et al. | 250/252.1 |

* cited by examiner

Primary Examiner — Jack Berman
Assistant Examiner — Eliza Osenbaugh-Stewart
(74) Attorney, Agent, or Firm — Slater & Matsil, LLP

(57) ABSTRACT

A method comprises directing an electron beam toward a sidewall of a three-dimensional region of a semiconductor device with a tilting angle and a first azimuth angle, detecting a first projection distance of the sidewall through a detector placed over the semiconductor device, directing the electron beam toward the sidewall with the tilting angle and a second azimuth angle, detecting a second projection distance of the sidewall, calculating a height of the three-dimensional region using a first function, wherein the first function includes the first tilting angle, the first azimuth angle, the second azimuth angle and the projection distance of the sidewall and calculating a sidewall edge of the three-dimensional region using a second function, wherein the second function includes the first azimuth angle, the second azimuth angle and the projection distance of the sidewall.

20 Claims, 6 Drawing Sheets

THREE-DIMENSIONAL SEMICONDUCTOR IMAGE RECONSTRUCTION APPARATUS AND METHOD

This application claims the benefit of U.S. Provisional Application No. 61/846,950, filed on Jul. 16, 2013, entitled "Three-Dimensional Semiconductor Image Reconstruction Apparatus and Method," which application is hereby incorporated herein by reference.

BACKGROUND

The ability to accurately and quickly obtain three dimensional (3D) imaging and 3D metrology is beneficial for integrated circuit manufacturing processes, particularly for devices having substantial topography such as fin-FET devices. Conventional methods to obtain 3D imaging include optical imaging, transmission electron microscopy (TEM), and the like. Such techniques have shortcomings however. As but one example, optical imaging techniques generally require the use of optical models, which can take weeks to build. TEM techniques are destructive as they require cross-sectioning the device to be imaged.

What is needed in the art are techniques that overcome the shortcomings of the prior art.

BRIEF DESCRIPTION OF THE DRAWINGS

For a more complete understanding of the present disclosure, and the advantages thereof, reference is now made to the following descriptions taken in conjunction with the accompanying drawings, in which.

Corresponding numerals and symbols in the different figures generally refer to corresponding parts unless otherwise indicated. The figures are drawn to clearly illustrate the relevant aspects of the various embodiments and are not necessarily drawn to scale.

DETAILED DESCRIPTION OF ILLUSTRATIVE EMBODIMENTS

The making and using of the present embodiments are discussed in detail below. It should be appreciated, however, that the present disclosure provides many applicable inventive concepts that can be embodied in a wide variety of specific contexts. The specific embodiments discussed are merely illustrative of specific ways to make and use the disclosure, and do not limit the scope of the disclosure.

The present disclosure will be described with respect to embodiments in a specific context, namely a three-dimensional semiconductor image reconstruction apparatus and method for manufacturing a FinFET. The invention may also be applied, however, to a variety of semiconductor devices.

Figure 1:
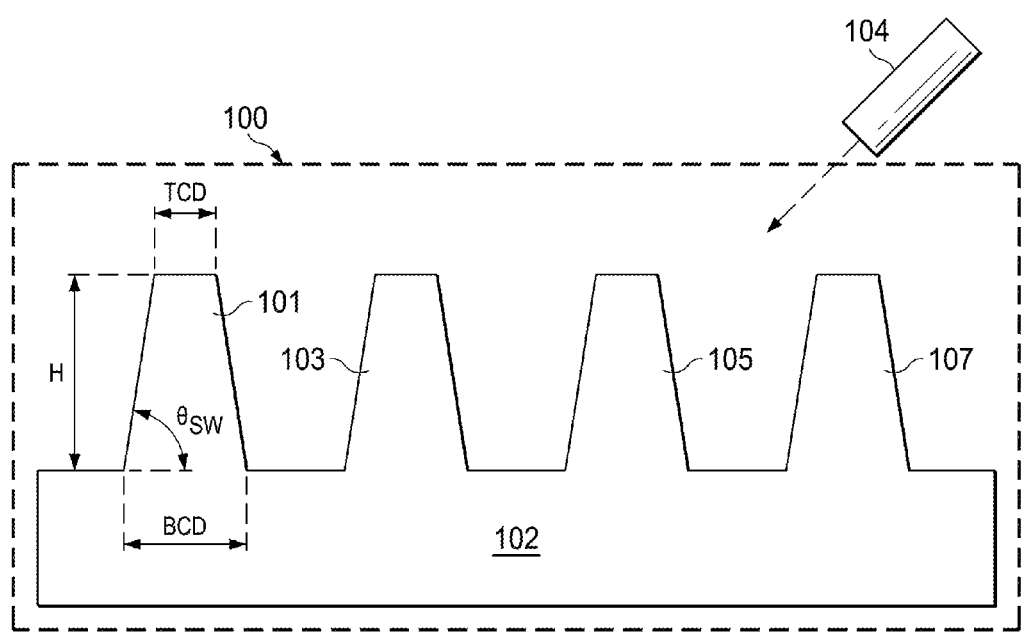
FIG. 1 illustrates a cross sectional view of a semiconductor device in accordance with various embodiments of the present disclosure.

FIG. 1 illustrates a cross sectional view of a semiconductor device in accordance with various embodiments of the present disclosure. The semiconductor device 100 may comprise four FinFETs (e.g., fin regions 101, 103, 105 and 107) formed over a substrate 102. The substrate 102 may be a silicon substrate. Alternatively, the substrate 102 may comprise other semiconductor materials such as germanium, compound semiconductor materials such as silicon carbide, gallium arsenide, indium arsenide, indium phosphide and the like. In accordance with an embodiment, the substrate 102 may be a crystalline structure. In accordance with another embodiment, the substrate 102 may be a silicon-on-insulator (SOI) substrate.

Each FinFET (e.g., fin region 101) shown in FIG. 1 is of a trapezoidal shape from a cross sectional view. The width of the top side of the trapezoidal shape is defined as TCD (a.k.a. Top Critical Dimension) and the width of the bottom side of the trapezoidal shape is defined as BCD (a.k.a. Bottom Critical Dimension). The height of the trapezoidal shape is defined as H as shown in FIG. 1. The sidewall and the bottom side of the trapezoidal shape form an angle, which is defined as $\theta_{SW}$ as shown in FIG. 1. The actual values of TCD, BCD, H and $\theta_{SW}$ are determined by the design rules and scale of the semiconductor process being used.

The trapezoidal fins may be partially enclosed by an isolation region (not shown). In accordance with an embodiment, the isolation region may be a shallow trench isolation (STI) structure. The STI structures may be fabricated by using suitable techniques including photolithography and etching processes. In particular, the photolithography and etching processes may comprise depositing a commonly used mask material such as photoresist over the substrate 102, exposing the mask material to a pattern and etching the substrate 102 in accordance with the pattern. In this manner, a plurality of openings may be formed as a result. The openings are then filled with dielectric materials to form the STI structures. A chemical mechanical polishing (CMP) process is then performed to remove excess portions of the dielectric materials, and the remaining portions are the isolation region.

An electron beam 104 is employed to measure the dimensions of the semiconductor device 100. As described above, the semiconductor device 100 is of a variety of three-dimensional topographic features. The electron beam 104 may be generated from a scanning electron microscopy (SEM) apparatus (not shown), which is placed over the semiconductor device 100 according to some embodiments.

The electron beam 104 may scan across the top surface of the semiconductor device 100. The electrons strike the topographic features such as the fins (e.g., fin region 101) of the semiconductor device 100. Various scattered electrons are generated through the electron-topographic feature interaction. Such scattered electrons are detected by a detector (not shown but illustrated in FIG. 2). Based upon the detected electrons, a processor (not shown) may reconstruct three-dimensional images for the three-dimensional features.

It should be noted that in order to have a high quality three-dimensional image, the SEM apparatus may have a plurality of fixed apertures and fixed detectors. It should further be noted that the SEM apparatus is capable of reconstructing three-dimensional images for a variety of topographic features such as a top critical dimension (CD) of a FinFET, a bottom CD of the FinFET, sidewall angles, the thickness and roughness of the sidewall, any combinations thereof and/or the like.

The detailed process of measuring three-dimensional topographic features and reconstructing three-dimensional images of the three-dimensional topographic features will be described below in detail with respect to FIGS. 2-8.

Figure 2:
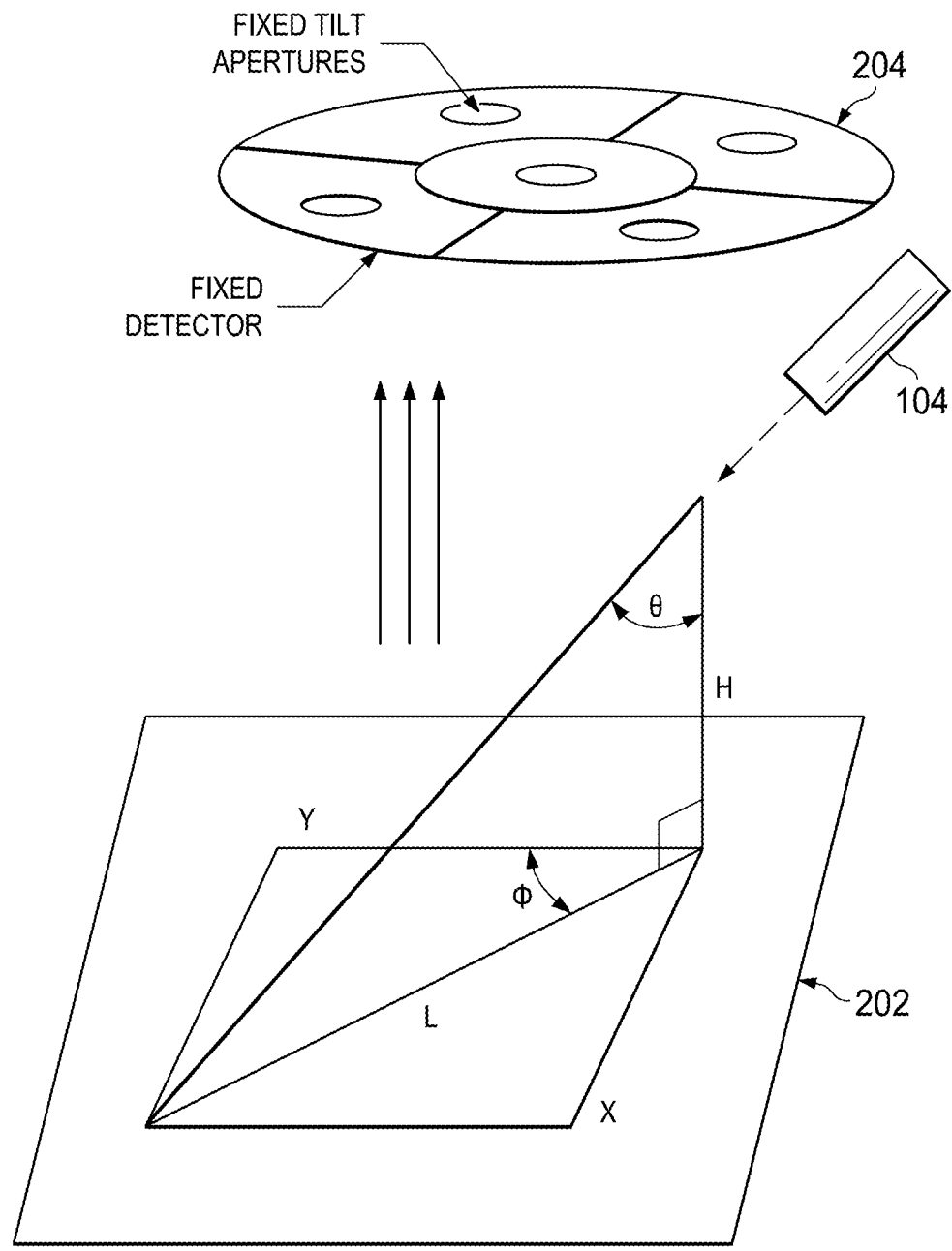
FIG. 2 illustrates a tilting angle and an azimuth angle of an electron beam and a fixed detector in accordance with various embodiments of the present disclosure.

FIG. 2 illustrates a tilting angle and an azimuth angle of an electron beam and a fixed detector in accordance with various embodiments of the present disclosure. The three-dimensional object may be the fin (e.g., fin region 101) shown in FIG. 1. As shown in FIG. 2, the three-dimensional object may be of a height H measured from a two-dimensional plane 202. An electron beam 104 is directed toward the sidewall of the three-dimensional object with a tilting angle θ. As a result, the height of the three-dimensional object is projected onto the two-dimensional plane 202 to produce a two-dimensional projection image L as shown in FIG. 2. The two-dimensional coordinates of the two-dimensional projection image L are X and Y respectively. As shown in FIG. 2, the two-dimensional projection image L and the vertical axis form an azimuth angle θ.

FIG. 2 further illustrates a fixed multi-directional side-view detector 204. The fixed multi-directional side-view detector 204 is placed over the device-under-test (DUT). The fixed multi-directional side-view detector 204 is part of a scanning electron microscope (SEM) apparatus. After the electrons strike the sidewall of the three-dimensional object, scattered electrons are detected by the fixed multi-directional side-view detector 204 as indicated by the arrows in FIG. 2.

As shown in FIG. 2, there may be a plurality of fixed multi-directional apertures on the fixed multi-directional side-view detector 204. In some embodiments, the fixed multi-directional apertures may be tilted apertures.

Figure 3:
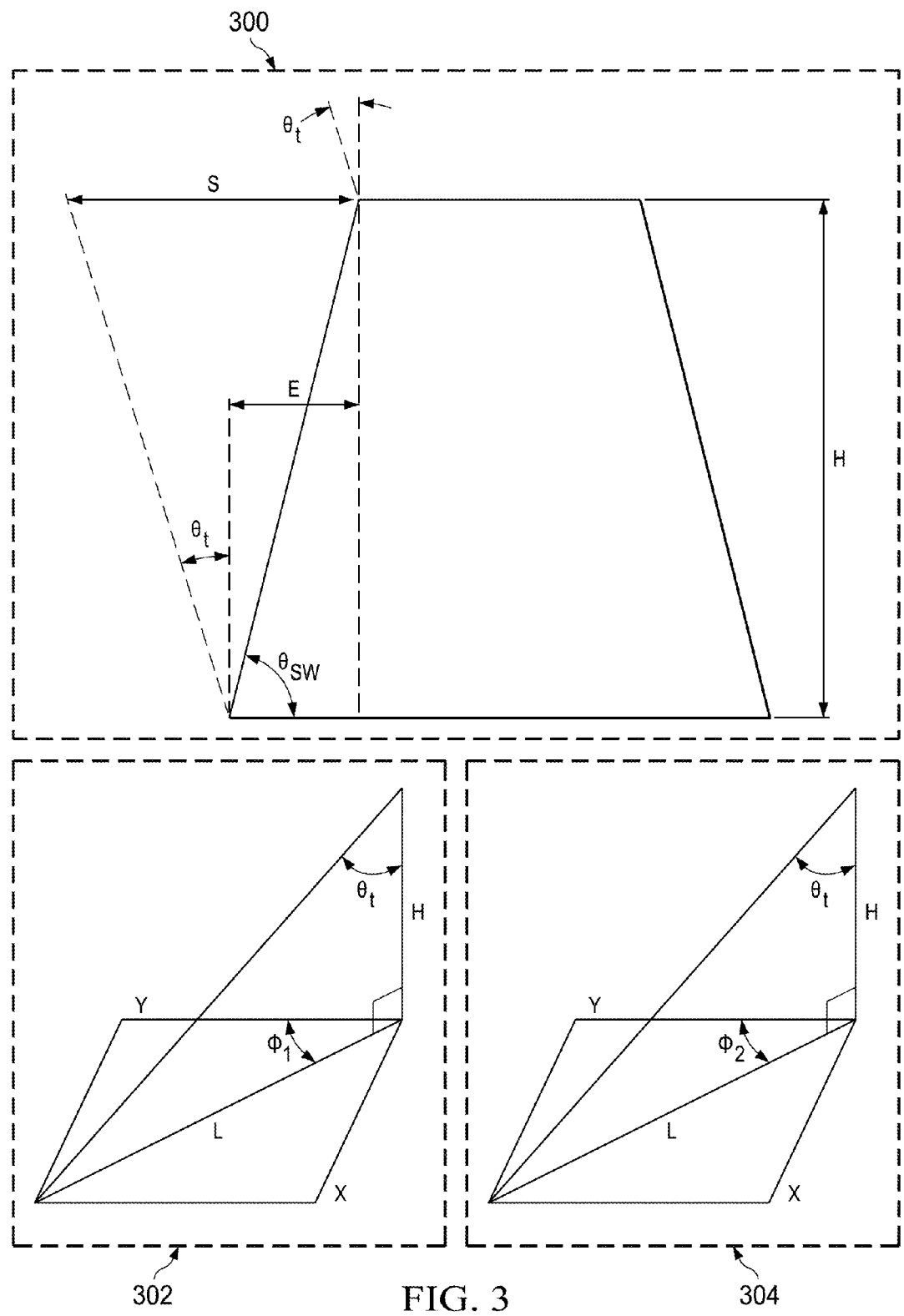
FIG. 3 illustrates a method of measuring a sidewall edge and a height of a three-dimensional object in accordance with various embodiments of the present disclosure.

FIG. 3 illustrates a method of measuring a sidewall edge and a height of a three-dimensional object in accordance with various embodiments of the present disclosure. The three-dimensional object 300 shown in FIG. 3 is similar to the fin region shown in FIG. 1, hence is not described in detail herein to avoid repetition.

FIG. 3 further illustrates two projection images 302 and 304. The projection images 302 and 304 are similar to that shown in FIG. 2. As shown in FIG. 3, the projection image 302 is of a first azimuth angle $\phi_1$ and the projection image 304 is of a second azimuth angle $\phi_2$. According to an embodiment, the azimuth angle $\phi$ and the tilting angle θ may satisfy the following equation:

$$\tan(\theta_t) \cdot \cos(\phi) = (S-E)/H \quad (1)$$

The three-dimensional object may be measured under two different azimuth angles (first azimuth angle $\phi_1$ and second azimuth angle $\phi_2$). As a result, the value of S may be given as $S_1$ and $S_2$ under two different azimuth angles. S1 and S2 are the projection distances of the sidewall of the three-dimensional object under two different azimuth angles. The values of S1 and S2 can be obtained from the SEM apparatus. Based upon equation (1) shown above, $S_1$ and $S_2$ can be expressed as:

$$S_1 = E - H \cdot \tan(\theta_t) \cdot \cos(\phi_1) \quad (2)$$

$$S_2 = E - H \cdot \tan(\theta_t) \cdot \cos(\phi_2) \quad (3)$$

The height of the three-dimensional object can be obtained through substitution. In other words, E in Equation (2) can be replaced by the E in Equation (3). The height of the three-dimensional object can be given as:

$$H = \frac{S_2 - S_1}{\tan(\theta_t) \cdot (\cos(\phi_1) - \cos(\phi_2))} \quad (4)$$

Likewise, the sidewall edge E of the three-dimensional object can be obtained through substitution. The sidewall edge E can be given as:

$$E = \frac{S_2 \cdot \cos(\phi_1) - S_1 \cdot \cos(\phi_2)}{(\cos(\phi_1) - \cos(\phi_2))} \quad (5)$$

Figure 4:
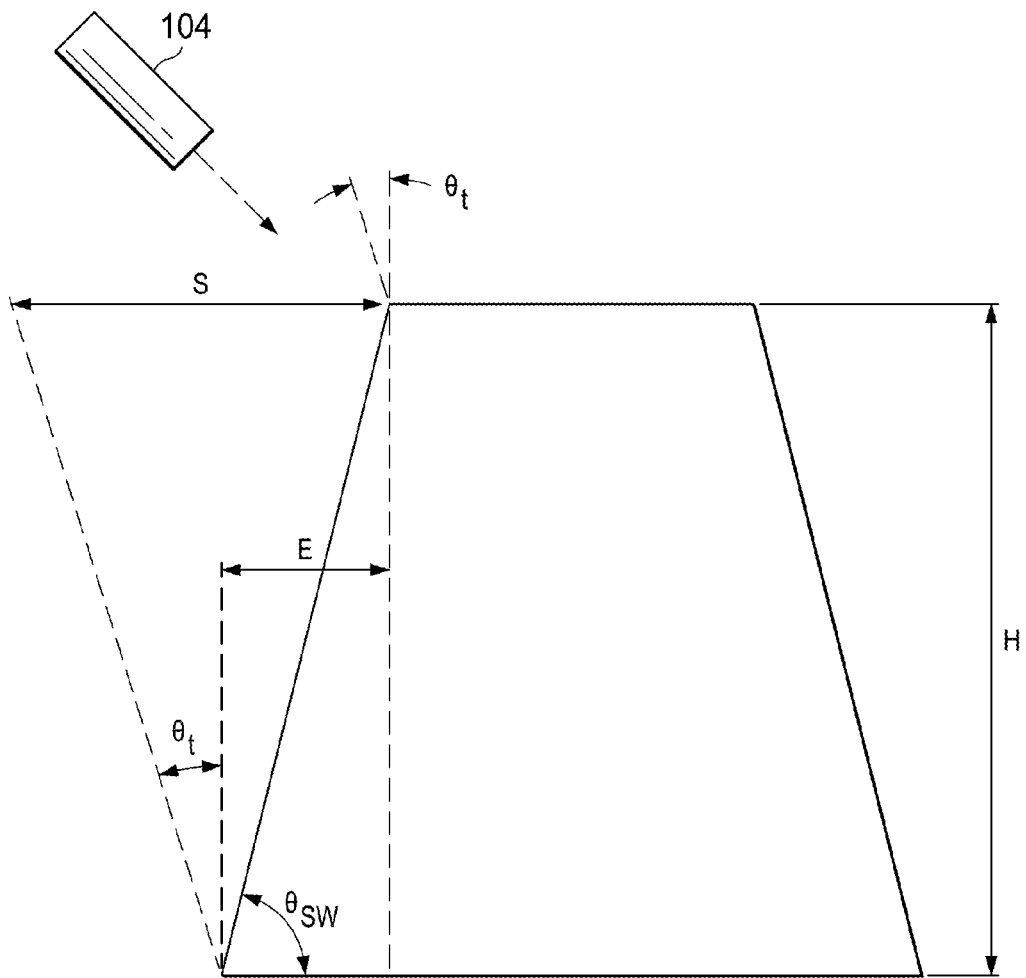
FIG. 4 illustrates a method of measuring a sidewall angle of a three-dimensional object in accordance with various embodiments of the present disclosure.

FIG. 4 illustrates a method of measuring a sidewall angle of a three-dimensional object in accordance with various embodiments of the present disclosure. The three-dimensional object may be the fin shown in FIG. 1. As shown in FIG. 4, the three-dimensional object may be of a sidewall angle $\theta_{sw}$ formed by a sidewall and a bottom side of the trapezoidal shape shown in FIG. 4.

An electron beam 104 is directed toward the sidewall of the trapezoidal shaped object with a tilting angle $\theta_t$ as shown in FIG. 4. The scattered electrons may be detected by a detector (not shown). The projection distance of the sidewall is defined as S, which can be obtained from the SEM apparatus.

The dimensions of the three-dimensional object can be reconstructed through stereographic imaging. More particularly, as shown in FIG. 4, the sidewall angle $\theta_{sw}$ can be determined by the following equation:

$$\tan(\theta_{SW}) = H/E \quad (6)$$

The tilting angle $\theta_t$ can be determined by the following equation:

$$\tan(\theta_t) = (S-E)/H \quad (7)$$

The sidewall angle $\theta_{sw}$ can be expressed as the following by replacing the height H shown in equation (6) with that shown in equation (7).

$$\theta_{SW} = \tan^{-1}(H/(S - H \cdot \tan(\theta_t))) \quad (8)$$

The method of calculating the height H and the sidewall edge E of the three-dimensional object has been described above with respect to FIG. 3, and hence both the height H and S are known values for calculating the sidewall angle $\theta_{sw}$.

Figure 5:
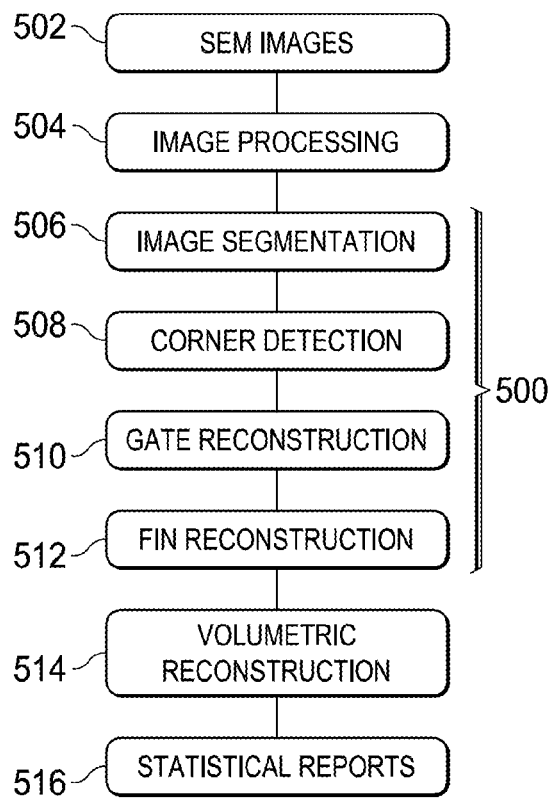
FIG. 5 illustrates a flow chart of reconstructing three-dimensional images of three-dimensional topographic features in accordance with various embodiment of the present disclosure.

FIG. 5 illustrates a flow chart of reconstructing three-dimensional images of three-dimensional topographic features in accordance with various embodiment of the present disclosure. The method begins at step 502. At step 502, a plurality of SEM images and their corresponding data may be obtained through the methods described above with respect to FIGS. 2-4.

At step 504, an image pre-processing process may be applied to the data of the SEM images. More particularly, a filtering algorithm and/or an image enhancement algorithm may be employed to improve the image quality of the SEM images. In particular, some important image characteristics such as contrast, brightness and the like may be improved through such an image pre-processing process. In some embodiments, the image enhancement may include an edge enhancement, which may be carried out through a filtering technique.

At step 506, in order to differentiate one topographic feature from others, a suitable image segmentation mechanism such as a grayscale signal analysis algorithm may be employed to automatically detect topographic features such as boundary detection, edge detection and/or the like.

In accordance with some embodiments, each topographic feature may be of a grayscale image value. After receiving the data representing the SEM images, the grayscale signal analysis algorithm may analyze the grayscale values of the data so as to differentiate different pattern groups.

At step 508, in order to detect the corner of a three-dimensional feature, a gradient based algorithm is employed to differentiate a corner from other topographic features. In some embodiments, the gradient magnitude of a corner may be higher compared to its adjacent points. As such, by calculating the gradient values of the data of the SEM images, the corner can be detected through finding a plurality of local maxima points.

At step 510, through the algorithm described at step 506, various regions including a poly gate of a FinFET may be identified. In addition, the physical characteristics such as the height of the poly gate may be obtained through the equations described above with respect to FIGS. 2-4. As a result, the poly gate can be reconstructed based upon the calculation shown in FIGS. 2-4.

At step 512, a three-dimensional region such as a fin region may be identified. The physical characteristics such as the height of the fin region may be obtained through the equations described above with respect to FIGS. 2-4. As a result, the fin region can be reconstructed based upon the physical characteristics.

Steps 506, 508, 510 and 512 are collectively called step 500 as shown in FIG. 5. Throughout the description, step 500 is alternative referred to as the three-dimensional image kernel.

At step 514, after obtaining each point's data, the three-dimensional topographic features of the whole region of the semiconductor device may be reconstructed accordingly using a volumetric reconstruction mechanism.

At step 516, a statistical report may be generated based upon the reconstruction of the images the three-dimensional topographic features of the whole region of the semiconductor device. The statistical report may include important characteristics of a FinFET such as top critical dimension, bottom critical dimension, height, sidewall angle, etching residues, roughness, thickness and/or the like.

It should be noted that the flow chart in FIG. 5 is merely an example, which should not unduly limit the scope of the claims. One of ordinary skill in the art would recognize many variations, alternatives, and modifications. For example, various step as illustrated in the flow chart of FIG. 5 may added, removed, replaced, rearranged, repeated, overlapped, and/or partially overlapped.

Figure 6:
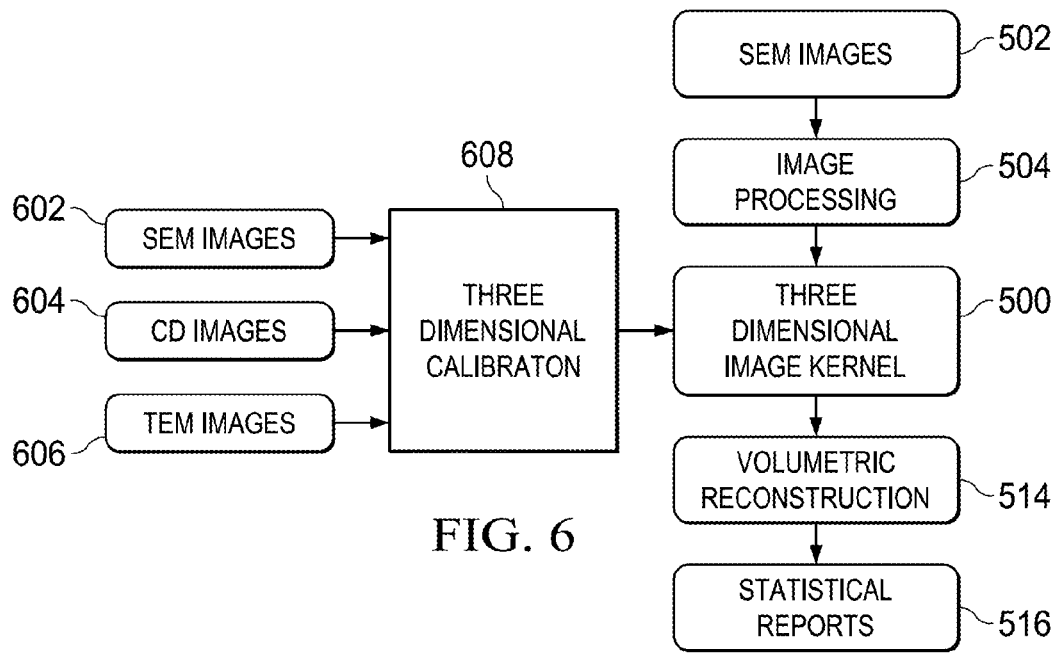
FIG. 6 illustrates a calibration flow chart of reconstructing three-dimensional topographic features in accordance with various embodiment of the present disclosure.

FIG. 6 illustrates a calibration flow chart of reconstructing three-dimensional topographic features in accordance with various embodiment of the present disclosure. The steps 502, 504, 514 and 516 are similar to those shown in FIG. 5, and hence are not discussed in detail herein.

Step 500 is the three-dimensional image kernel. Step 500 includes various functions of reconstructing three-dimensional topographic features such as the image segmentation of step 506, the corner detection algorithm of step 508, the poly gate reconstruction algorithm of step 510 and the fin reconstruction algorithm of step 512. In order to calibrate the algorithms so as to a high quality image, images obtained from other mechanisms may function as a benchmark to fine-tune the algorithms included in step 500.

As shown in FIG. 6, the images 602 from the SEM based method described above, the images 604 from an optical critical dimension apparatus and the images 606 from a transmission electron microscope (TEM) are fed into a three-dimensional calibration apparatus 608.

In some embodiments, the images generated by the optical critical dimension apparatus may be of a high resolution top view of three-dimensional topographic features. The TEM images may be of a high resolution in X-direction and Z-direction. The three-dimensional calibration apparatus 608 compares the SEM images 602 with the optical CD images 604 and the TEM images 606. More particularly, the three-dimensional calibration apparatus 608 may analyze the pitch structures of the SEM images 602 and find the pitch deviations in comparison with the optical CD images 604 and the TEM images 606.

Based upon the comparison results above, the three-dimensional calibration apparatus 608 may fine-tune the algorithms in the three-dimensional image kernel 500 accordingly until the SEM images 602 show a good agreement with the optical CD images 604 and the TEM images 606.

It should be noted that the flow chart in FIG. 6 is merely an example, which should not unduly limit the scope of the claims. One of ordinary skill in the art would recognize many variations, alternatives, and modifications. For example, various step as illustrated in the flow chart of FIG. 6 may added, removed, replaced, rearranged, repeated, overlapped, and/or partially overlapped.

Figure 7:
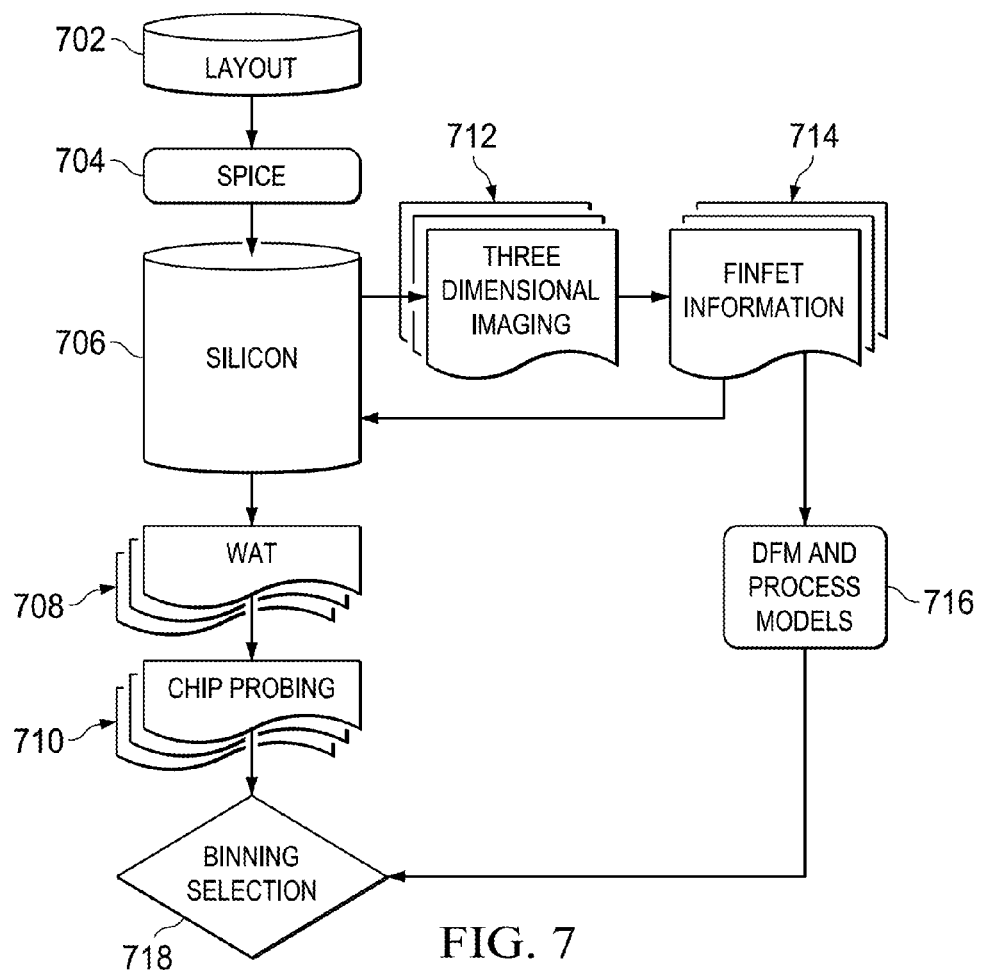
FIG. 7 illustrates a flow chart of applying the method shown in FIG. 5 to various semiconductor manufacturing processes in accordance with various embodiment of the present disclosure.

FIG. 7 illustrates a flow chart of applying the method shown in FIG. 5 to various semiconductor manufacturing processes in accordance with various embodiment of the present disclosure. At step 702, a layout of an Integrated Circuit (IC) is loaded into a processor before the IC is sent to an IC manufacturer. The layout includes a variety of physical parameters of the IC, such as the dimensions of a fin region of a FinFET.

At step 704, in order to evaluate the device characteristics before sending the layout to the semiconductor manufacturer, the layout of the IC is provided to a simulation tool (e.g., Simulation Program with Integrated Circuit Emphasis (SPICE) and/or the like) for modeling electrical parameters of the IC. The electrical parameters may include saturation currents, leakage currents, threshold voltages and/or the like.

At step 706, the layout is sent to a semiconductor manufacturer, wherein a semiconductor wafer is fabricated through various fabrication steps such as doping/ion implantation, etching, deposition, lithographic patterning and/or the like.

At step 708, the wafer undergoes a wafer acceptance test (WAT), wherein the wafer is a device-under-test (DUT) placed on a test structure. At step 710, the wafer may be placed on a wafer chuck and tested by a probe card. The probe card test of the wafer may be alternatively referred to as chip probing through which various function defects of the wafer may be identified before the wafer is sliced into individual packages.

At step 712, the three-dimensional images of the wafer are generated based upon the methods shown in FIGS. 2-5. In addition, at step 714, physical dimensions such as height, top CD, bottom CD and the like may be obtained through the algorithms shown in FIG. 5. The physical dimensions are fed into various design and manufacture processes such as design for manufacturability (DFM) models (e.g., step 716), wafer fabrication steps (e.g., step 706) and electrical characterization processes (e.g., step 708).

At step 716, DFM models are generated based upon the FinFET information of step 714. The DFM models are an integration of manufacturing data and design procedure for better yield and reliability. The DFM models require IC manufacturers to provide manufacturing information. The FinFET information obtained at step 714 may help to obtain enhanced DFM models.

At step 718, the chip probing results at step 712 and the DFM models at step 714 may provide electrical characteristics of the wafer. As a result, a bin is selected and the wafer may undergo subsequent fabrication steps.

Figure 8:
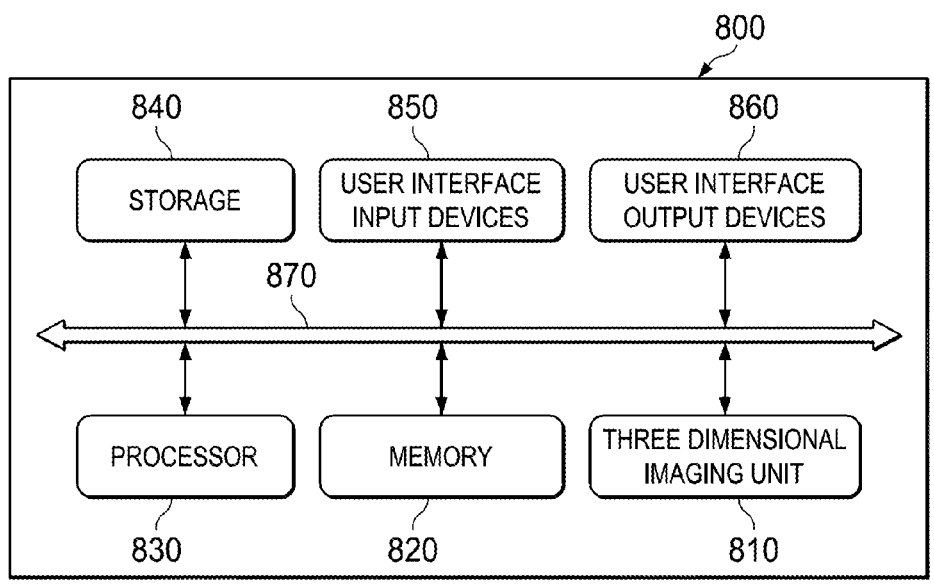
FIG. 8 illustrates a simplified block diagram of a computer system 800 that can be used to implement the three-dimensional reconstruction method in accordance with various embodiments of the present disclosure.

FIG. 8 illustrates a simplified block diagram of a computer system 800 that can be used to implement the three-dimensional semiconductor image reconstruction method in accordance with various embodiments of the present disclosure. The computer system 800 includes a three-dimensional image reconstruction unit 810, a memory 820, a processor 830, a storage unit 840, network interface input devices 850, network interface output devices 860 and a data bus 870.

It should be noted that this diagram is merely an example of a personal computer, which should not unduly limit the scope of the claims. Many other configurations of a personal computer are within the scope of this disclosure. One of ordinary skill in the art would also recognize the three-dimensional semiconductor image reconstruction method may be performed by other computer systems including a portable computer, a workstation, a network computer, or the like.

The three-dimensional image reconstruction unit 810 may be a physical device, a software program, or a combination of software and hardware such as an Application Specific Integrated Circuit (ASIC). In accordance with an embodiment, when the computer receives a data file through the network interface input devices 850, the processor 830 loads the data file into the storage unit 840. According to an embodiment where the three-dimensional image reconstruction method is implemented as a software program, the processor 830 loads the software program from the storage unit 840 and operates it in the memory 820. After the processor 830 performs the steps of FIG. 5, the processor 830 sends the results to the end user through a network interface output devices 860.

In accordance with an embodiment, a device comprises a semiconductor device having at least one three-dimensional region protruding over a two-dimensional plane and a scanning electron microscope system including a fixed electron beam aperture, a side view detector and an electron beam directed toward the semiconductor device with a tilting angle.

In accordance with an embodiment, a method comprises directing an electron beam toward a sidewall of a three-dimensional region of a semiconductor device with a tilting angle and a first azimuth angle, detecting a first projection distance of the sidewall through a detector placed over the semiconductor device, directing the electron beam toward the sidewall of the three-dimensional region of the semiconductor device with the tilting angle and a second azimuth angle, detecting a second projection distance of the sidewall through the detector placed over the semiconductor device, calculating a height of the three-dimensional region using a first function, wherein the first function includes the first tilting angle, the first azimuth angle, the second azimuth angle and the projection distance of the sidewall and calculating a sidewall edge of the three-dimensional region using a second function, wherein the second function includes the first azimuth angle, the second azimuth angle and the projection distance of the sidewall.

In accordance with an embodiment, a method comprises applying a scanning electron microscope process to a three-dimensional region of a semiconductor device, applying a data enhancement process to detected data from the scanning electron microscope process, detecting different regions of the semiconductor device from the detected data and measuring dimensions of the semiconductor device.

Although embodiments of the present disclosure and its advantages have been described in detail, it should be understood that various changes, substitutions and alterations can be made herein without departing from the spirit and scope of the disclosure as defined by the appended claims.

Moreover, the scope of the present application is not intended to be limited to the particular embodiments of the process, machine, manufacture, composition of matter, means, methods and steps described in the specification. As one of ordinary skill in the art will readily appreciate from the present disclosure, processes, machines, manufacture, compositions of matter, means, methods, or steps, presently existing or later to be developed, that perform substantially the same function or achieve substantially the same result as the corresponding embodiments described herein may be utilized according to the present disclosure. Accordingly, the appended claims are intended to include within their scope such processes, machines, manufacture, compositions of matter, means, methods, or steps.

What is claimed is:

1. A method comprising:
directing an electron beam toward a sidewall of a three-dimensional region of a semiconductor device with a tilting angle and a first azimuth angle;
detecting a first projection distance of the sidewall through a detector placed over the semiconductor device;
directing the electron beam toward the sidewall of the three-dimensional region of the semiconductor device with the tilting angle and a second azimuth angle;
detecting a second projection distance of the sidewall through the detector placed over the semiconductor device;
calculating a height of the three-dimensional region using a first function, wherein the first function includes the first tilting angle, the first azimuth angle, the second azimuth angle and the projection distance of the sidewall; and
calculating a sidewall edge of the three-dimensional region using a second function, wherein the second function includes the first azimuth angle, the second azimuth angle and the projection distance of the sidewall.

2. The method of claim 1, further comprising:
calculating a sidewall angle of the three-dimensional region using a third function, wherein the third function includes the tilting angle, the height of the three-dimensional region and the projection distance of the sidewall.

3. The method of claim 2, wherein the third function is:

$$\theta_{SW} = \tan^{-1}(H/E)$$

where $\theta_{SW}$ is the sidewall angle of the three-dimensional region, H is the height of the three-dimensional region and E is the sidewall edge of the three-dimensional region.

4. The method of claim 1, wherein the first function is:

$$H = \frac{S_2 - S_1}{\tan(\theta_t) \cdot (\cos(\phi_1) - \cos(\phi_2))}$$

where H is the height of the three-dimensional region, $S_1$ is the first projection distance of the sidewall, $S_2$ is the second projection distance of the sidewall, $\theta_t$ is the tilting angle, $\Phi_1$ is the first azimuth angle and $\Phi_2$ is the second azimuth angle.

5. The method of claim 1, wherein the second function is:

$$E = \frac{S_2 \cdot \cos(\phi_1) - S_1 \cdot \cos(\phi_2)}{(\cos(\phi_1) - \cos(\phi_2))}$$

where E is the sidewall edge of the three-dimensional region, $S_1$ is the first projection distance of the sidewall, $S_2$ is the second projection distance of the sidewall, $\Phi_1$ is the first azimuth angle and $\Phi_2$ is the second azimuth angle.

6. The method of claim 1, further comprising:
directing the electron beam toward the sidewall of the three-dimensional region through a fixed electron beam aperture.

7. The method of claim 1, further comprising:
detecting scattered electrons through a fixed detector over the semiconductor device.

8. The method of claim 1, wherein:
the semiconductor is a FinFET; and
the three-dimensional region is a fin region of the FinFET.

9. A method comprising:
directing an electron beam toward a sidewall of a three-dimensional object with a first tilting angle and a first azimuth angle;
measuring a first projection distance of the sidewall of the three-dimensional object;
directing the electron beam toward the sidewall of the three-dimensional object with a second tilting angle and a second azimuth angle;
measuring a second projection distance of the sidewall of the three-dimensional object; and
calculating a height of the three-dimensional object, a sidewall edge of the three-dimensional object and a sidewall angle based upon the first tilting angle, the first azimuth angle, the second tilting angle, the second azimuth angle, the first projection distance and the second projection distance.

10. The method of claim 9, wherein:
the first tilting angle is equal to the second tilting angle.

11. The method of claim 10, further comprising:
calculating the height of the three-dimensional object using:

$$H = \frac{S_2 - S_1}{\tan(\theta_t) \cdot (\cos(\phi_1) - \cos(\phi_2))}$$

where H is the height of the three-dimensional object, $S_1$ is the first projection distance, $S_2$ is the second projection distance, $\theta_t$ is the first tilting angle equal to the second tilting angle, $\Phi_1$ is the first azimuth angle and $\Phi_2$ is the second azimuth angle.

12. The method of claim 10, further comprising:
calculating the sidewall edge of the three-dimensional object using:

$$E = \frac{S_2 \cdot \cos(\phi_1) - S_1 \cdot \cos(\phi_2)}{(\cos(\phi_1) - \cos(\phi_2))}$$

where E is the sidewall edge of the three-dimensional object, $S_1$ is the first projection distance, $S_2$ is the second projection distance, $\Phi_1$ is the first azimuth angle and $\Phi_2$ is the second azimuth angle.

13. The method of claim 9, further comprising:
calculating the sidewall angle of the three-dimensional object using:

$$\theta_{SW} = \tan^{-1}(H/E)$$

where H is the height of the three-dimensional object, E is the sidewall edge of the three-dimensional object.

14. The method of claim 9, wherein:
the three-dimensional object is a semiconductor fin.

15. A method comprising:
directing an electron beam toward a sidewall of a semiconductor fin with a tilting angle and a first azimuth angle;
measuring a first projection distance of the sidewall of the semiconductor fin;
directing the electron beam toward the sidewall of the semiconductor fin with the tilting angle and a second azimuth angle;
measuring a second projection distance of the sidewall of the semiconductor fin; and
calculating a height of the semiconductor fin and a sidewall edge of the semiconductor fin based upon the tilting angle, the first azimuth angle, the second azimuth angle, the first projection distance and the second projection distance.

16. The method of claim 15, further comprising:
calculating a sidewall angle of the semiconductor fin based upon the sidewall edge of the semiconductor fin and the height of the semiconductor fin.

17. The method of claim 16, further comprising:
calculating the sidewall angle of the semiconductor fin using:

$$\theta_{SW} = \tan^{-1}(H/E)$$

where $\theta_{SW}$ is the sidewall angle of the semiconductor fin, H is the height of the semiconductor fin and E is the sidewall edge of the semiconductor fin.

18. The method of claim 15, wherein:
the semiconductor fin is of a trapezoidal shape.

19. The method of claim 15, further comprising:
generating the electron beam from a scanning electron microscopy apparatus.

20. The method of claim 15, wherein:
the semiconductor fin is enclosed by an isolation region and protrudes over the isolation region.

* * * * *